United States Patent
Doiron et al.

[11] Patent Number: 6,058,937
[45] Date of Patent: May 9, 2000

[54] PHOTODYNAMIC THERAPY OF HIGHLY VASCULARIZED TISSUE

[75] Inventors: Daniel R. Doiron, Santa Ynez; Leslie A. Edwards, Santa Barbara, both of Calif.

[73] Assignee: Miravant Systems, Inc., Santa Barbara, Calif.

[21] Appl. No.: 08/897,258

[22] Filed: Jul. 18, 1997

[51] Int. Cl.$^7$ .................................................. A61B 19/00
[52] U.S. Cl. .......................................... 128/898; 514/185
[58] Field of Search ..................... 424/423, 427, 424/443, 445, 449–50; 514/21, 145, 183, 185, 410, 465, 472; 530/359; 128/898; 604/19, 20, 51, 52; 606/2; 534/11, 15

[56] References Cited

U.S. PATENT DOCUMENTS

| | | | |
|---|---|---|---|
| 5,214,036 | 5/1993 | Allison et al. | 514/185 |
| 5,368,841 | 11/1994 | Trauner et al. | 514/183 |
| 5,576,013 | 11/1996 | Williams et al. | 424/423 |
| 5,775,339 | 7/1998 | Woodburn et al. | 128/898 |

*Primary Examiner*—Mickey Yu
*Assistant Examiner*—Kelly O'Hara
*Attorney, Agent, or Firm*—Bryan Cave LLP

[57] ABSTRACT

A method for intraoperatively administering Photodynamic Therapy (PDT) to a highly vascularized target tissue. The method of PDT begins with the introduction of an exogenous photosensitizing agent into the target tissue-associated vasculature. Upon entry of the photosensitizer into the vasculature, the target tissue is immediately exposed to phototherapeutic light having a wavelength suitable for photoactivating the photosensitizer within the target tissue-associated vasculature. Continued illumination of the target tissue affects destruction of the vasculature within the tissue without requiring the photosensitizer to accumulate within the nonvascular tissue cells prior to photoactivation. The destruction of the vasculature supplying the target tissue destroys the target tissue. The method eliminates the prior art procedural step of waiting for the photosensitive compound to accumulate within the target tissue cells prior to administering photoactivating light to the target tissue. The photodynamic treatment of Dysfunctional Uterine Bleeding is presented as an example of applying the method to treat highly vascularized target tissue. The intraoperative method may be adapted for treating other tissues by increasing the amount of photosensitizer laden blood in the tissue by adjunctive means such as inducing localized vasodilator.

4 Claims, 1 Drawing Sheet

PHOTODYNAMIC THERAPY OF HIGHLY VASCULARIZED TISSUE

BACKGROUND OF THE INVENTION

1. Field of the Invention

This invention relates to a method for administering Photodynamic Therapy to a highly vascularized tissue.

2. Prior Art

Photodynamic Therapy, PDT, is the treatment of diseased, usually hyper proliferative tissue using photosensitizing chemicals and light. PDT, as presently used, is based on the observation that certain photosensitizing compounds preferentially concentrate in hyperproliferating tissue relative to most other normal tissues. A well known example of a procedure which exploits this differential concentration of photosensitizer is the use of PDT to treat tumors. This preferential concentration, or therapeutic ratio as it is sometimes called, is the basis of obtaining the potential therapeutic selectivity that is usually desired in the clinical application of PDT. This is generally obtained by first administering the photosensitizer by a suitable route, generally intravenously, then waiting for some period of time for the photosensitizer to be accumulated within the target tissues while most nontarget tissue eliminate the photosensitizer. The reason for this selective affinity and retention of photosensitizers in hyperproliferating tissue is not presently known but support for the observation has been documented for a variety of photosensitizers and hyperproliferating tissue.

In most cases, the therapeutic response of PDT includes both cellular and vascular effects. PDT, in accordance with current clinical practice, requires the procedural step of allowing a period of time to elapse after injection of a photosensitizer into the blood stream to permit the photosensitizers to accumulate in a tissue. The countdown, the elapsed time required for accumulation prior to administering phototherapeutic light, begins upon introduction of the photodynamically active photosensitizer into the patient's circulatory system. With time, the photosensitizer is taken up by tissue(s) and tissue components and bound thereto. While utilization of this preferential, differentially selective photosensitizer uptake/retention by hyperproliferating tissue is effective for a variety of photosensitizers and target tissues, due to uptake throughout the body and elimination, the delay time necessary for the accumulation of a therapeutically effective concentration of photosensitizer in the tissue generally requires the use of a relatively high photosensitizer dose. This high level of drug, in turn, can lead to problems such as systemic and local toxicity and prolonged photosensitivity of the skin. In addition, this methodology does not specifically target vasculature but focuses instead on the selective ability of a target tissue (a tissue to be treated by PDT), to take up and retain photosensitizers from the blood.

In summary, in the art, PDT is generally used to treat hyperproliferating tissues, i.e. cancer, by first administering a photosensitizer to the patient by a suitable route such as by intravenous [IV], intramuscular [IM], intraperitoneal [IP] injection or oral administration, and then waiting for a predetermined period of time known, a priori to be sufficient to effect the preferential uptake and retention of the photosensitizer in the target tissue relative to the concentration of the photosensitizer in normal (non-hyperproliferating) tissues. By permitting time to elapse after systemic administration of the drug, the photosensitizer is generally localized in a variety of tissue/cell types as well as locations within the target tissue. The time for photosensitizer build-up in a target tissue varies but is in the range of 2–24 h. The resulting therapeutic response therefore generally involves a variety of cytological effects.

A recent exception to the procedure summarized above is the use of PDT to treat the retinal neovasculature related to a form of Age Related Macular Degeneration. In this therapeutic procedure, the photosensitizer is administered IV and the therapeutic light is applied selectively to the neovascular area within the eye a short time afterward. The leakiness of the vasculature due to the fragile and permeable nature of the neovasculature in the eye, causes a large quantity of fluid to pool in the immediate vicinity of the neovasculature. The pooled, localized extravascular fluid contains a significant amount of photosensitizer. Upon photoactivation, tissue destruction within the neovascular area is enhanced due to the abundance of the photosensitizer therewithin relative to the neighboring tissue which lacks such neovasculature and the concomitant accumulation of fluid therearound.

SUMMARY OF THE INVENTION

A method for administering photodynamic treatment to tissues, abnormal or normal, which have, or can be induced to have, a high blood derived fluid volume to tissue ratio. The method shortens the time required for administering PDT to a tissue and is applicable to a variety of therapeutic applications of PDT, such as the treatment of Benign Prostatic Hyperplasia, highly vascularized tumors, and high density vascular disorders. This method may be appropriate for treatment of disorders in hollow organs or cavities in the body, for example, the bladder, esophagus, uterus, gastrointestinal tract and the oral cavity. It may be appropriate for treatment of specitfic disorders such as Dysfunctional Uterine Bleeding, Barrett's disease, Benign Prostatic Hyperplasia, erythroplakia and leucoplakia. A particular therapeutic application of the method for treatment of Dysfunctional Uterine Bleeding, [DUB] is presented as an example.

The invention provides a method for administering PDT to a tissue which encompasses the following procedural steps:

(1) injecting an efficient photodynamically active photosensitizing compound intravenously; then (2) immediately exposing the blood permeated target tissue to phototherapeutic light having a wavelength appropriate for the activation of the photosensitizer in the circulation; then (3) continuing delivery of phototherapeutic light to the target tissue until a therapeutic dosage of light is delivered sufficient to effect the destruction of the vasculature of the target tissue and before the photosensitizer is substantially removed from the circulation.

It is an objective of this invention to provide an improved method for intraoperatively administering Photodynamic Therapy to highly vascularized tissue.

It is a primary object of the invention to provide a method for administering photodynamic therapy to tissue, which is selective for the tissue, and wherein the time required for administering Photodynamic Therapy is substantially reduced relative to current procedures.

It is another object of this invention to provide an intraoperative method for treating Dysfunctional Uterine Bleeding by Photodynamic Therapy which reduces the amount of time required for treating a patient.

The features of the invention believed to be novel are set forth with particularity in appended claims. However, the invention itself, both as to organization and method of operation, together with further objects and advantages thereof may best be understood by reference to the following description in conjunction with the accompanying drawing:

DESCRIPTION OF THE PREFERRED METHOD

Figure 1:
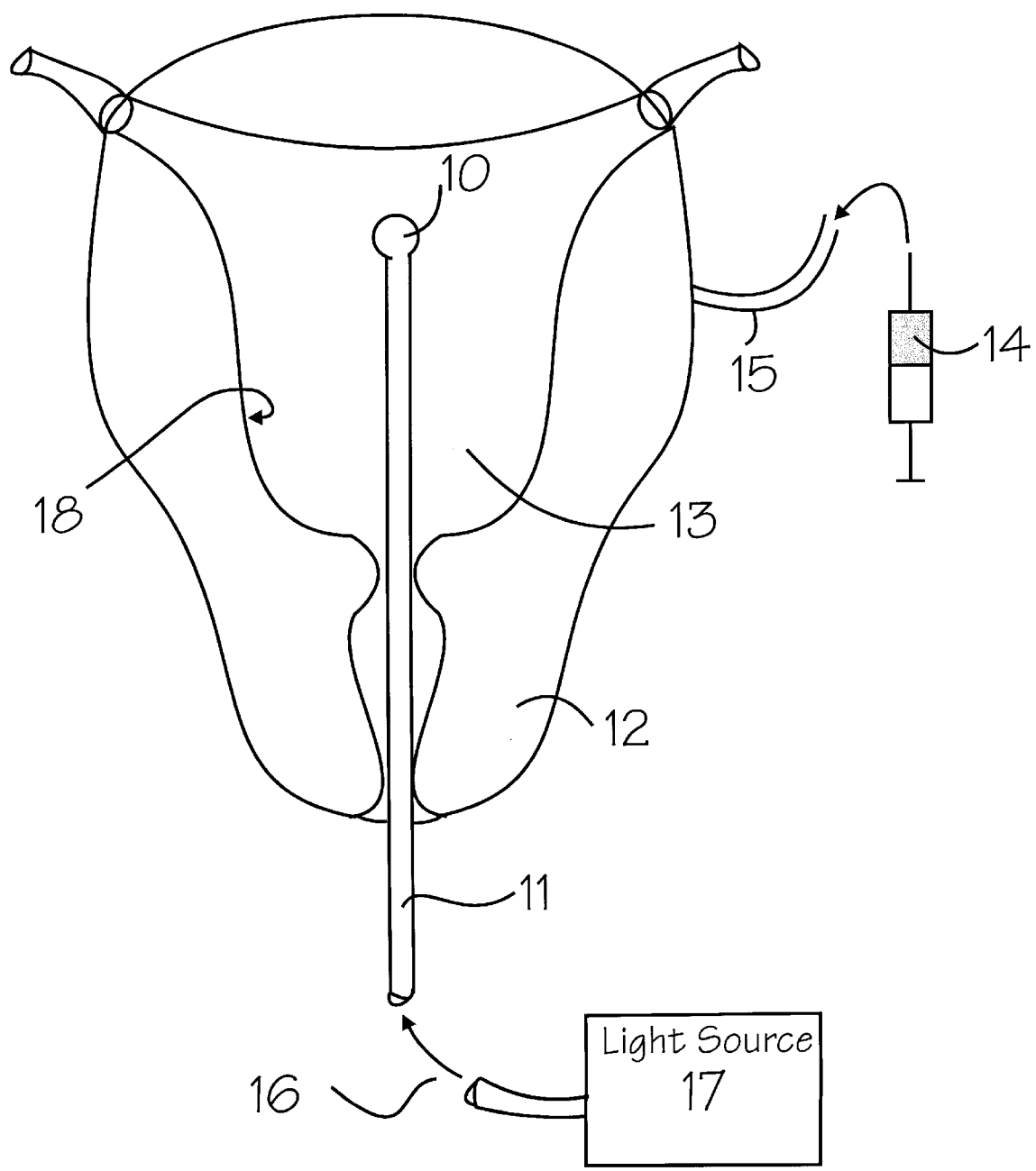
FIG. 1 is a schematic diagram of a light delivery catheter inserted within the uterus for administering Photodynamic Therapy to the vasculature within the endometrium-associated vasculature.

The method of performing PDT in accordance with the present invention is conveniently presented by means of an example such as the treatment of Dysfunctional Uterine Bleeding (DUB). DUB is a significant clinical problem in many pre-menopausal women and is one of the leading reasons for performing hysterectomies. The endometrium affects the normal menstrual cycle. When the normal menstrual cycle is disrupted such as by hormonal imbalance and/or endometrial hyperplasia, the resulting vaginal bleeding can be extreme and continuous leading to significant clinical and medical problems. If hormonal therapy does not control the condition it is necessary to use an alternative form of interventional therapy to either completely cease or at least control the DUB. One such alternative intervention is the performance of a hysterectomy. A hysterectomy is not only costly but has potential for significant complications and morbidity due to its surgical nature. Other methods are under development for destroying the endometrium, and to some extent the myometrium, such that the menstrual cycle is disrupted and therefore the DUB. This has been done by direct chemical necrosis of the uterine lining, thermally heating the uterine tissue with energy such as from lasers, electrocautery, microwaves, etc. and potentially freezing the endometrium.

PDT is being developed for endometrial ablation by a number of academic and commercial groups. The approach used in accordance with the teachings of the prior art is significantly different than the procedures of the method disclosed in the present invention. The prior art use of PDT employs procedural steps for treating DUB which are identical to the "inject-wait-illuminate" procedures of PDT used for treating tumors and hyperproliferating tissue outlined above. In accordance with the prior art PDT treatment of DUB, time is allowed to pass to allow the photosensitizer to accumulate in the endometrial and myometrial tissue prior to photoactivation of the photosensitizer. For IV and oral administration, the time required for accumulation is usually from 4 to 24 hours, while for intravesical administration, the accumulation time is from 3 to 8 hours. After such delay times the photosensitizer is not localized only in the dense vasculature of the myometrium and endometrium but is distributed throughout the body tissues. In some cases (such as when a photosensitizer precursor is administered to produce protoporphyrin IX in vivo as the photosensitizer) the actual target tissue is not the vasculature but instead the glandular components of the tissue. With such broad distribution of the photosensitizer, and its potential nonvasculature localization, application of the activating light may not lead to significant penetration and destruction of the endometrium and therefore result in recurrence of the DUB. Such responses have been noted in both preclinical animal and early clinical testing of PDT treatment of DUB using the concept of long delay between photosensitizer and light administration. In addition, these long delay time methods require the use of significantly greater delivered doses of photosensitizer to obtain the desired therapeutic response due to the potential whole body redistribution of the photosensitizer during the delay time.

FIG. 1 illustrates the scheme for performing PDT to treat DUB, the distal end of a light delivery catheter 11 comprising an optical waveguide is advanced through the cervix 12 until positioned within the uterine cavity 13. A photosensitive drug 14 is administered IV into a block vessel 15 supplying or draining the uterine tissue. Substantially immediately thereafter, therapeutic light 16 from a source of light 17 is conducted via the catheter 11 to the distal end 10 thereof which distal end is adapted to provide uniform illumination to the surrounding uterine wall 18. An inflatable balloon (not shown) may be interposed between the distal end 10 of the catheter 11 and the uterine wall 18, or the uterine cavity 13 may be inflated with a gas to avoid compressing the vasculature. The fluence required for phototherapy may be determined preoperatively and is in the range 10–150 Joules/cm$^2$. The treatment time will, therefore, depend on the irradiance of the uterine wall which depends upon the power output of the catheter, geometrical considerations and drug dose as will be discussed below.

In the present invention, a low dose of photosensitizer is administered intravenously to a patient. An exemplary (partial) list of such photosensitizer compounds is presented in Table 1. Immediately or a short time after injection, minutes not hours, the photosensitizer activating light is delivered to illuminate the intrauterine wall. The method permits the selective destruction of the vasculature of the endometrium using a low dose of light because the light is delivered during the time of maximum photosensitizer concentration in the endometrial vasculature. Destruction of the tissue-associated vasculature down to the myometrium assures that the endometrium will not regenerate thereby permanently eliminating the DUB.

TABLE 1 pyrrole-derived macrocyclic compounds
porphyrins and derivatives thereof
chlorins and derivatives thereof
bacteriochlorins and derivatives thereof
isobacteriochlorins and derivatives thereof
phthalocyanines and derivatives thereof
naphthalocyanines and derivatives thereof
porphycenes and derivatives thereof
porphycyanines and derivatives thereof
pentaphyrin and derivatives thereof
sapphyrins and derivatives thereof
texaphyrins and derivatives thereof
phenoxazine dyes and derivatives thereof
phenothiazines and derivatives thereof
chaloorganapyrylium dyes and derivatives thereof
triarylmethanes and derivatives thereof
rhodamines and derivatives thereof
fluorescenes and derivatives thereof
azaporphyrins and derivatives thereof
benzochlorins and derivatives thereof
purpurins and derivatives thereof
chlorophylls and derivatives thereof
verdins and derivatives thereof Proof of this concept has been established in a rat animal model by comparing the ability to cause necrosis of the endometrium of the animal using the photosensitizer tin etiopurpurin (SnET2) and 664 nm red light either at 15 minutes post injection or 24 hours post injection. The rat uterine wall is composed of three layers, as it is in humans, the endometrium is the layer that is closest to the lumen. It is composed of highly vascular glandular tissue. The layer adjacent to the endometrium is the myometrium. It is composed of smooth muscle. The outer layer that composes the serosa is the parametrium. In studies performed in rats, a treatment interval of 15 minutes provides responses as follows:

At a fixed light dose of 150 J/cm (375 J/cm$^2$), a transmural response (absolute cytologic damage from the inner layer to the outer layer) was observed at drug doses of 2, 1, 0.5 and 0.25 mg/kg. At a drug dose of 0.125, a specific response in the form of tissue destruction occurred. At a fixed drug dose of 0.5 mg/kg., a consistent transmural response at light doses of 200 j/cm$^2$ and 100 J/cm$^2$ was observed and endometrial selective responses were observed at 50 J/cm$^2$. At the lower drug dose of 0.25 J/cm$^2$, endometrial specific responses occurred at 100 to 75 J/cm$^2$.

In summary, it was found that at 24 hours post injection, with the classical PDT treatment methodology, the amount of SnET2 and light needed was quite high and it was difficult to get well controlled and repeatable endometrial ablation. For light application 15 minutes after SnET2 injection, it was determined that only $\frac{1}{20}^{th}$ of the drug dose was required for tissue necrosis. In addition, a lower light dose (100 J/cm$^2$ as compared to 350 J/cm$^2$) was required to obtain tissue necrosis which was highly controllable and repeatable. A significantly lower light dose may be used requiring only a slightly higher drug dose.

The shortened treatment time offered by the method has significant potential impact on the potential for using PDT for the treatment of DUB and other intrauterine disorders as well as other tissue disorders. The method permits administration of both lower injected photosensitizer doses and light doses while providing selective destruction of the target vasculature, even if the tissue is not hyperproliferative and/or normal. Such lower drug doses minimize potential complications due to the photosensitizer, for example skin photosensitivity, while making the procedure cheaper.

While particular embodiments of the present invention have been illustrated and described, it would be obvious to those skilled in the art that various other changes and modifications can be made without departing from the spirit and scope of the invention. For example, a tissue targeted to receive PDT may be treated in such a way that the amount of photosensitizer-laden blood or blood-derived fluid present within the tissue is intraoperatively increased thereby increasing the amount of photosensitizer within the tissue-associated vasculature. It is therefore intended to cover the appended claims all such changes and modifications that are within the scope of this invention.

What we claim is:

1. A method for administering photodynamic therapy to a vascularized tissue located within or in contact with a hollow organ in the body of a patient comprising the steps of:
   (a) presenting a source of light, said source of light providing phototherapeutic light having a wavelength suitable for photoactivating a photosensitive compound; then
   (b) inflating the organ with gas; and
   (c) positioning said light source to be in optical communication with said vascularized tissue; then
   (d) introducing a dosage of said photosensitive compounds into a blood vessel supplying or draining said vascularized tissue within said patient; and
   (e) prior to or at completion of the step of introducing a dosage of said photosensitive compounds into said blood vessel, illuminating said vascularized tissue with said phototherapeutic light and continuing said illumination for a period of time sufficient to achieve a therapeutic effect.

2. The method of claim 1 wherein the step of inflating the organ with gas is accomplished by introduction of an inflatable gas receptacle.

3. A method for administering photodynamic therapy to a vascularized tissue located within or in contact with a cavity in the body of a patient comprising the steps of:
   (a) presenting a source of light, said source of light providing phototherapeutic light having a wavelength suitable for photoactivating a photosensitive compound; then
   (b) inflating the cavity with gas; and
   (c) positioning said light source to be in optical communication with said vascularized tissue; then
   (d) introducing a dosage of said photosensitive compounds into a blood vessel supplying or draining said vascularized tissue within said patient; and
   (e) prior to or at completion of the step of introducing a dosage of said photosensitive compounds into said blood vessel, illuminating said vascularized tissue with said phototherapeutic light and continuing said illumination for a period of time sufficient to achieve a therapeutic effect.

4. The method of claim 3 wherein the step of inflating the cavity with gas is accomplished by introduction of an inflatable gas receptacle.

* * * * *